US 8,298,179 B2

(12) United States Patent
Holman et al.

(10) Patent No.: US 8,298,179 B2
(45) Date of Patent: Oct. 30, 2012

(54) CATHETER ASSEMBLY WITH TAPERED JOINTS AND METHOD OF MANUFACTURE

(75) Inventors: Thomas J. Holman, Minneapolis, MN (US); Afsar Ali, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1917 days.

(21) Appl. No.: 11/020,540

(22) Filed: Dec. 22, 2004

(65) Prior Publication Data

US 2006/0135909 A1 Jun. 22, 2006

(51) Int. Cl.
*A61M 25/10* (2006.01)
(52) U.S. Cl. .................................. 604/103.06
(58) Field of Classification Search .................. 604/103, 604/103.06
See application file for complete search history.

(56) References Cited

U.S. PATENT DOCUMENTS

| | | | | |
|---|---|---|---|---|
| 4,251,305 A | | 2/1981 | Becker et al. .................... 156/86 |
| 4,395,806 A | * | 8/1983 | Wonder et al. ............ 29/890.122 |
| 4,913,701 A | | 4/1990 | Tower ............................. 604/103 |
| 4,943,278 A | | 7/1990 | Euteneuer et al. ............... 604/96 |
| 5,156,595 A | * | 10/1992 | Adams .......................... 606/194 |
| 5,279,561 A | | 1/1994 | Roucher et al. .................. 604/96 |
| 5,409,495 A | * | 4/1995 | Osborn ......................... 623/1.11 |
| 5,501,759 A | | 3/1996 | Forman ........................ 156/272.8 |
| 5,503,631 A | * | 4/1996 | Onishi et al. .............. 604/103.07 |
| 5,549,552 A | | 8/1996 | Peters et al. ..................... 604/96 |
| 5,899,882 A | * | 5/1999 | Waksman et al. ......... 604/103.07 |
| 6,129,707 A | * | 10/2000 | Cryer .......................... 604/96.01 |
| 6,575,934 B2 * | | 6/2003 | Duchamp ............... 604/102.02 |
| 6,702,802 B1 | | 3/2004 | Hancock et al. ............. 604/524 |
| 6,746,424 B2 * | | 6/2004 | Stamberg ................. 604/103.06 |
| 6,902,571 B2 * | | 6/2005 | Owens et al. ................. 606/194 |
| 6,953,470 B2 * | | 10/2005 | Holman et al. ............... 606/194 |
| 6,955,658 B2 | | 10/2005 | Murray, III |
| 6,960,186 B1 * | | 11/2005 | Fukaya et al. ........... 604/103.06 |
| 6,982,024 B2 * | | 1/2006 | Shkolnik ....................... 156/293 |
| 7,141,059 B2 * | | 11/2006 | Duchamp et al. ............. 606/194 |
| 2002/0008255 A1 | | 1/2002 | Noda et al. ............... 604/103.06 |
| 2004/0131808 A1 | | 7/2004 | Schoenle et al. |
| 2005/0131445 A1 * | | 6/2005 | Holman et al. ............... 606/194 |

FOREIGN PATENT DOCUMENTS

WO  WO 2006/068749 A1 *  6/2006

* cited by examiner

*Primary Examiner* — Nicholas Lucchesi
*Assistant Examiner* — Aarti B Berdichevsky
(74) *Attorney, Agent, or Firm* — Vidas, Arrett & Steinkraus, P.A.

(57) ABSTRACT

A catheter assembly comprises at least one catheter shaft and a balloon. The catheter shaft comprises a substantially cylindrical portion and at least one tapered portion. The tapered portion forms an angle with the cylindrical portion of about 1 degree to about 25 degrees. At least one of the waists of the balloon is sealingly engaged to the tapered portion.

3 Claims, 5 Drawing Sheets

CATHETER ASSEMBLY WITH TAPERED JOINTS AND METHOD OF MANUFACTURE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Medical catheters having a balloon mounted thereon are useful in a variety of medical procedures. Balloon catheters may be used to widen a vessel into which the catheter is inserted by dilating the blocked vessel, such as in an angioplasty procedure. Balloon catheters may also be used to expand and/or seat a medical device such as a stent or graft at a desired position within a body lumen. In all of these applications, fluid under pressure may be supplied to the balloon through an inflation lumen in the catheter, thereby expanding the balloon.

It is essential in the manufacture of balloon catheters to properly seal the balloon to the catheter. The seal must be able to withstand the high pressures to which it is subjected on inflation of the balloon. A poor seal may result in leakage of inflation fluid and inability to achieve the desired pressure or even rapid loss of pressure and deflation of the balloon.

A number of methods for sealing a balloon to a catheter are known in the art. Methods involving the use of a suitable adhesive to bond the balloon to the catheter tube are described in U.S. Pat. No. 4,913,701 and U.S. Pat. No. 4,943,278. The use of adhesives, however, adds to the thickness of the catheter and increase its rigidity at the region of the bonds.

Another such method, where heat fusible materials are employed, involves the application of heat to fuse the balloon to the catheter tube. To that end, resistance heating of copper jaws has been employed to fuse a balloon to a catheter tube. Resistance heating, however, can result in the formation of small, random channels at the balloon-catheter interface, potentially giving rise to undesirable variations in the strength of different bonds. Such heating can also cause undesirable crystallization and stiffening of the balloon and catheter material, not only at the bond site, but also in both directions axially of the bond, due to heat conduction through the balloon and the catheter, and heat radiation from the jaws.

A non-contact method for heat sealing a balloon onto a catheter is disclosed in U.S. Pat. No. 4,251,305 to Becker et al. A length of thin tubing is slid over an elongated shaft of the catheter and shrink tubing installed over the thin walled tubing at its ends overlapping the catheter shaft. The shrink tubing is partially shrunk. Lamps emitting energy along the visible and infrared spectra are used to provide radiant energy to form thermoplastic joints that bond the tubing and shaft. This method, nevertheless, suffers from the problem of undesired heat transfer along the catheter and balloon.

Yet another fusion-based method disclosed in U.S. Pat No. 5,501,759 to Forman involves the use of a beam of laser radiation to match an absorption characteristic of polymeric materials. The polymeric materials are melted by the radiation and then allowed to cool and solidify to form a fusion bond.

Another fusion-based method described in Forman involves the simultaneous use of multiple beams of energy to supply energy at discrete points about the circumference of the balloon and thereby heat the balloon. A single beam can be split into multiple beams and the multiple beams directed about the circumference of the balloon via fiber optics.

Figure 1:
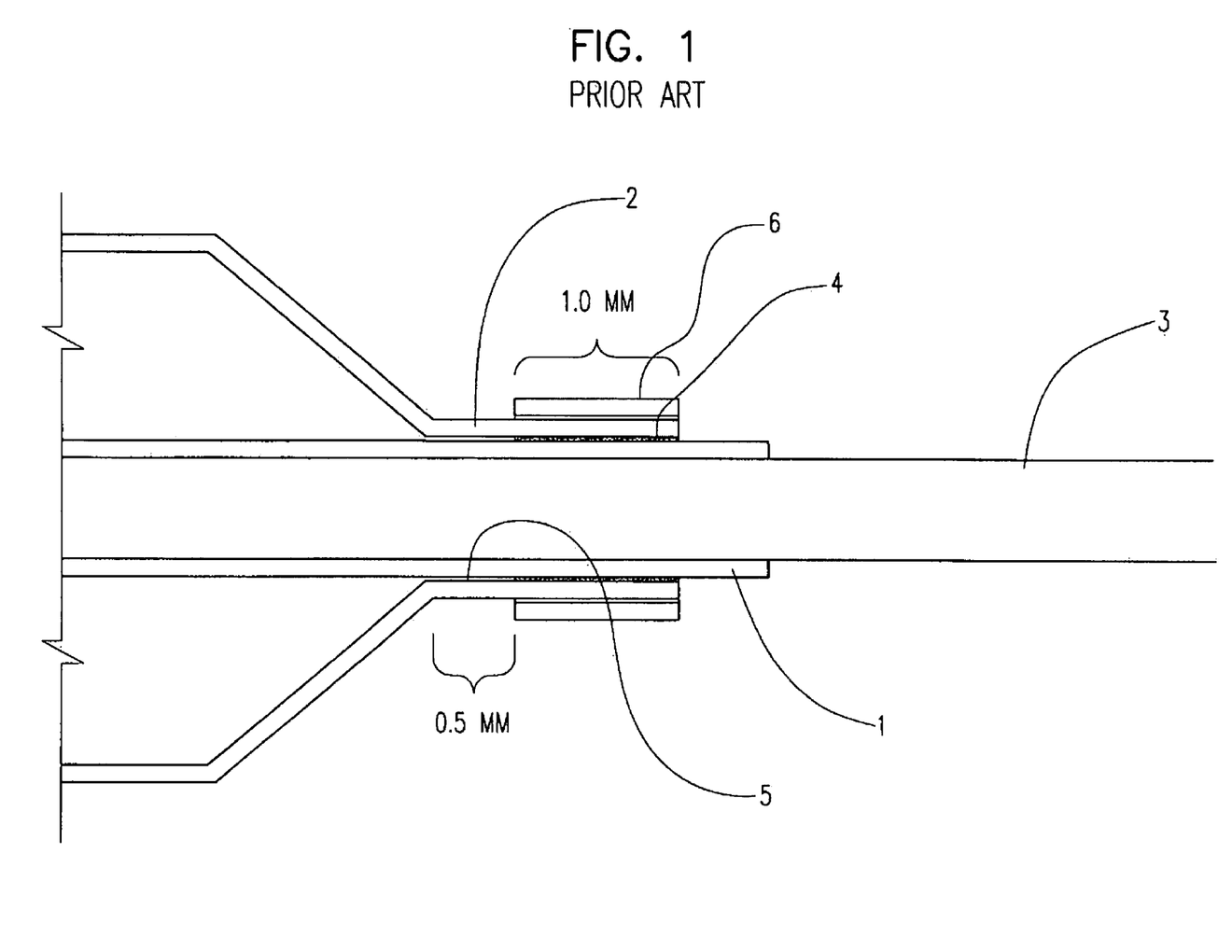
FIG. 1 illustrates a PRIOR ART catheter assembly process.

In many prior methods of manufacturing catheter assemblies, an example of which is illustrated in PRIOR ART FIG. 1, joint formation is accomplished by overlapping (e.g. a lap weld configuration) the components 1 and 2 to be joined on a mandrel 3 and heating a region of the overlapping components to form a weld or joint 4. Because the components are typically cylindrical in shape (or at least in the regions where they are to be joined) and inherently have differing diameters to accommodate their overlap, the components tend to form a space 5 therebetween. Such a space presents difficulties in maintaining proper and continuous engagement between the components during joint formation. To address this, a heat shrink 6 or other constricting device is thus used to force the components 1 and 2 together during heating. Where the components 1 and 2 are a catheter shaft and a balloon waist, typically the joint 4 is about 1 mm in length. To prevent inadvertent heating and possible damage to the balloon cone 6, approximately 0.5 mm of the waist 2 immediately adjacent to the cone 6 remains un-welded. This unjoined region of the catheter/balloon interface may contribute to joint failure during expansion of the balloon under pressure and present difficulties during the folding process.

In addition to the above, it is also noted that such prior manufacturing methods, also tend to provide a rather abrupt transition between the balloon and catheter shaft which may affect catheter flexibility, trackability, and/or cross-over performance of the resulting catheter assembly.

Thus, a need exists to provide a catheter with joints that not only are adequately sealed and resistant to bond failure, but which do not deter the overall performance of the catheter. A method of manufacturing such a catheter is also needed.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

At least one embodiment of the invention is directed to forming a joint between two or more overlapping components having a substantially conic or frusto-conical shape.

In at least one embodiment, the invention is directed to a catheter that utilizes a tapered or frusto-conical joint between one or more components. Some embodiments of the invention are directed to the manufacturing of catheters employing such tapered joints. The taper defined along the interface of the joined components allows the components to be in intimate or immediate contact prior to and during any subsequent bonding process such as heat or laser welding.

In at least one embodiment a region of a catheter shaft is provided with a tapered region. The tapered region defines an angle relative to the un-tapered region of the catheter shaft. The taper may vary in angle, direction and degree (extent) as desired. In at least one embodiment the angle is about 1 to about 7 degrees. In some embodiments the angle is about 10 degrees or less. In some embodiments the angle is about 25 degrees or less.

Where the catheter is a balloon catheter, the balloon is provided with a waist having a corresponding angle to that of the tapered region of the catheter shaft such that the waist and the tapered region are substantially parallel to one another when engaged.

In at least one embodiment the balloon waist is sealingly engaged to the tapered region by heat or laser welding to form a weld site. In some embodiments the balloon waist and the tapered region are joined together without the use of a heat shrink. In at least one embodiment the weld site is defined by the interface of the entire length of the balloon waist and the tapered region of the catheter shaft.

In some embodiments a cooling fluid is applied to the weld site during the welding process. In at least one embodiment the cooling fluid is liquid or gaseous $N_2$. In at least on embodiment the cooling fluid is a stream of cooled air.

In some embodiments the components of the catheter, which are to be joined together, may be optically clear relative to the wave-length of the laser light used to weld the components together. In such cases a site-specific layer of light absorbent material may be applied to and/or between the components to absorb the laser light and bring one or both components to their respective melting points along the weld site.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 3:
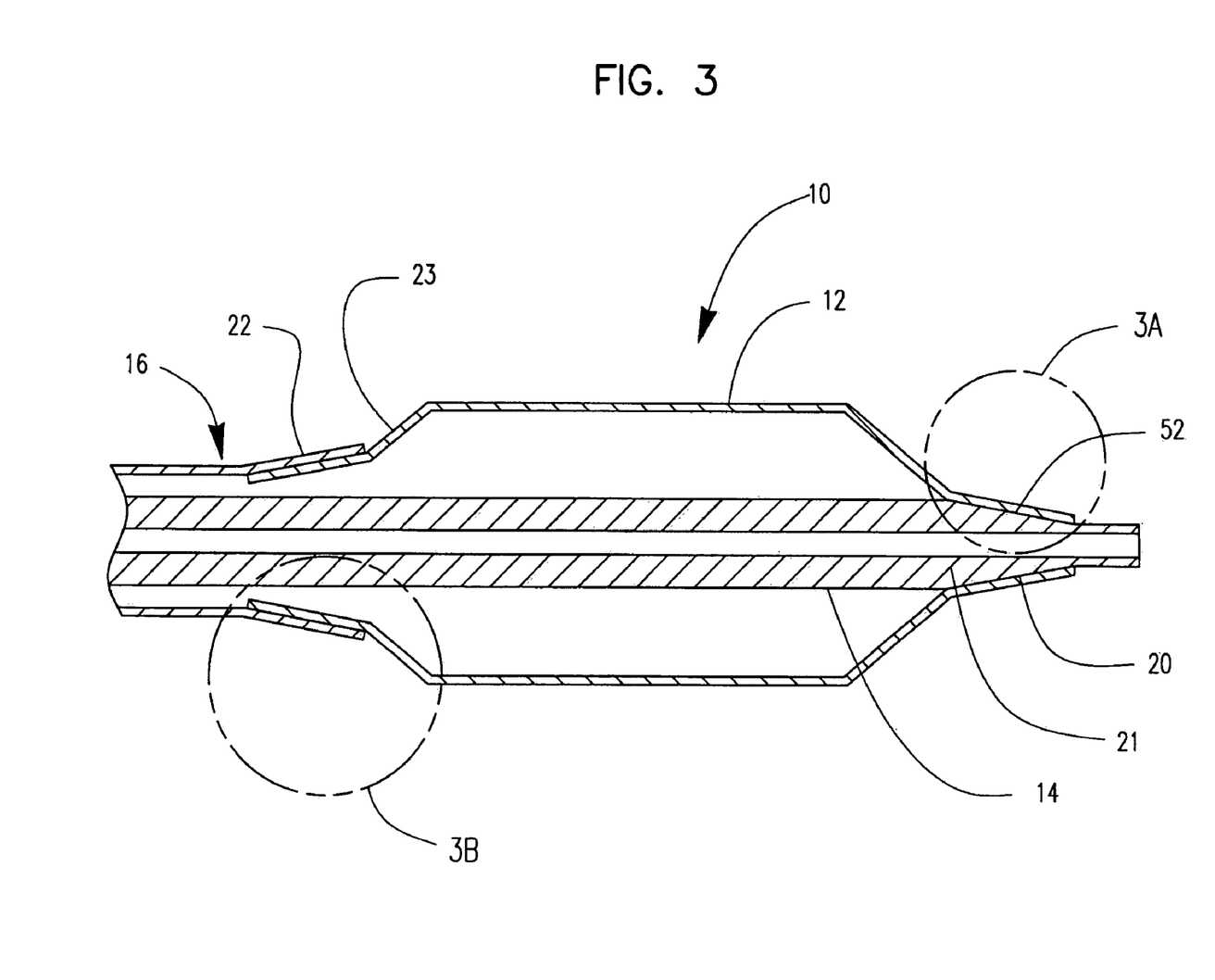
FIG. 3 is a longitudinal cross-sectional view of an embodiment of the invention including a catheter assembly having tapered joints.

In at least one embodiment, the present invention is directed to a balloon catheter, such as for example catheter 10 illustrated in FIG. 3, wherein the catheter is provided with one or more tapered engagement areas 20 and 22. Wherein the tapered configuration of the engagements areas 20 and 22 are in relation to the substantially cylindrical portions 21 and 23 of the respective catheter shafts 14 and 16. The tapered engagement areas 20 and 22 provide the catheter with areas where balloon waists 30 and 32 can be respectively engaged to provide the catheter 10 with a less abrupt transition between the balloon 12 and catheter shafts 14 and/or 16.

Balloon 12 may be any type of balloon. The balloon may be suitable for angioplasty, stent deliver or other uses. Where the balloon is used to deploy a stent the catheter 10 may also include a stent or similar implantable prosthesis, for implantation into a body vessel or lumen.

By providing the inner shaft 14 of the catheter 10 with a tapered or frusto-conical shaped engagement region 20 and likewise providing the balloon 12 with a distal waist 30 having a corresponding shape, the inner shaft 14 and the balloon waist 30 may be forced tightly together as a result of the self-locking tapered shape. In order for the components 14 and 30 to self-lock, the angle, indicated at reference numeral 100 in FIG. 3a, formed by the substantially cylindrical portion 21 of the shaft 14 and the taper or frusto-conical region 20 is preferably between about 1 and about 7 degrees. In some embodiments the angle 100 may be greater than 7 degrees. In at least one embodiment the angle is about 25 degrees of less.

Figure 2:
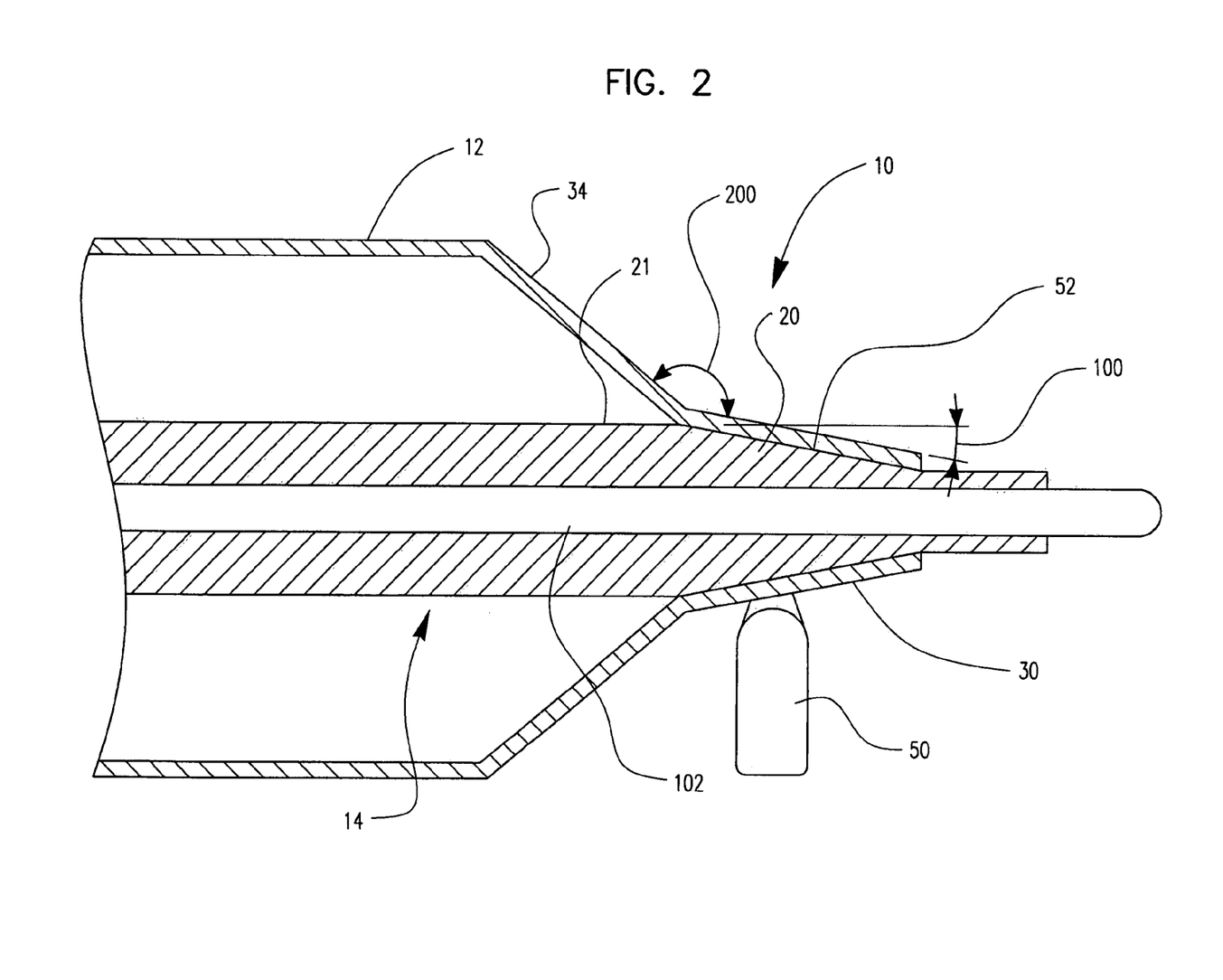
FIG. 2 is a partial longitudinal cross-sectional view of an embodiment of the invention comprising a catheter assembly shown during assembly.

Because of the self-locking aspect of the engagement region 20 and the distal balloon waist 30, there is no longer a need to utilize a heat shrink layer, such as is shown in PRIOR ART FIG. 1 to push the components together during welding such as is shown in FIG. 2. Instead, a laser or other heating mechanism 50 may be used to directly or indirectly (e.g. Through Transmission Laser Welding) heat the region 20 and/or distal waist 30 to form a joint, depicted as dotted-line 52 in FIG. 2, therebetween.

While a heat shrink material may be used, by avoiding the use of a heat shrink only that portion of the assembly to which is desired to be joined need be heated. As a result, the joint 52 may extend through the entire length of the balloon waist 30 thereby avoiding the presence of an unjoined region between the catheter shaft and balloon waist, such as is common in many prior catheter assemblies as illustrated in PRIOR ART FIG. 1, previously discussed.

As compared to a more traditional joint between cylindrical components 1 and 2, such as is shown in PRIOR ART FIG. 1, the use of a tapered joint 52, such as is shown in FIG. 2, provides the catheter 10 with an increase in the transition angle, indicated at reference numeral 200, between the distal cone 34 and the distal waist 30. Such an increased transition angle provides a narrower catheter profile in the area of the joint and provides the balloon with a more gradual and potentially less traumatic entrance profile.

Figure 3A:
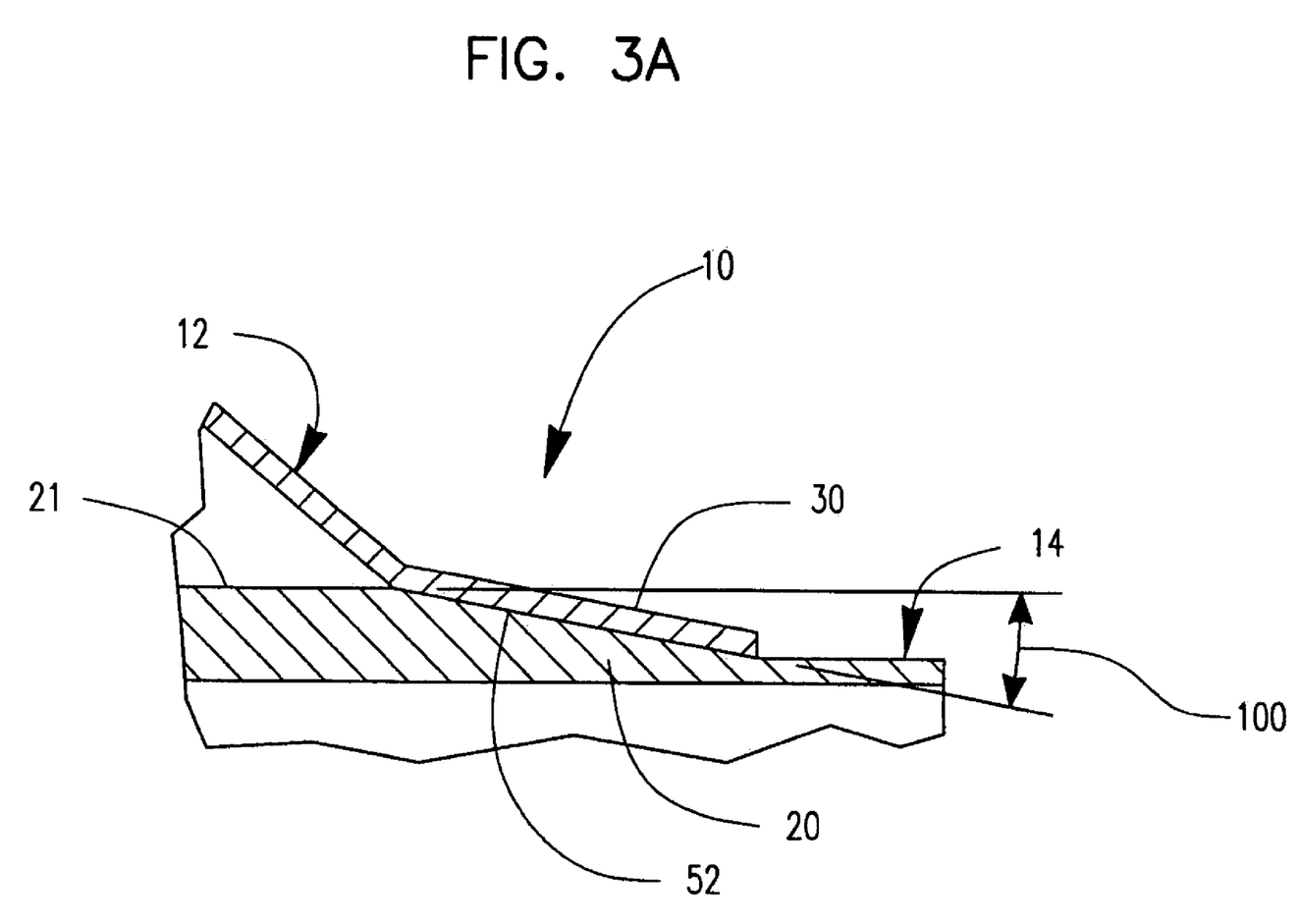
FIG. 3a is an enlarged view of a portion of the catheter assembly shown in FIG. 3 wherein the joint between an inner catheter shaft and the distal balloon waist is illustrated.
Figure 3B:
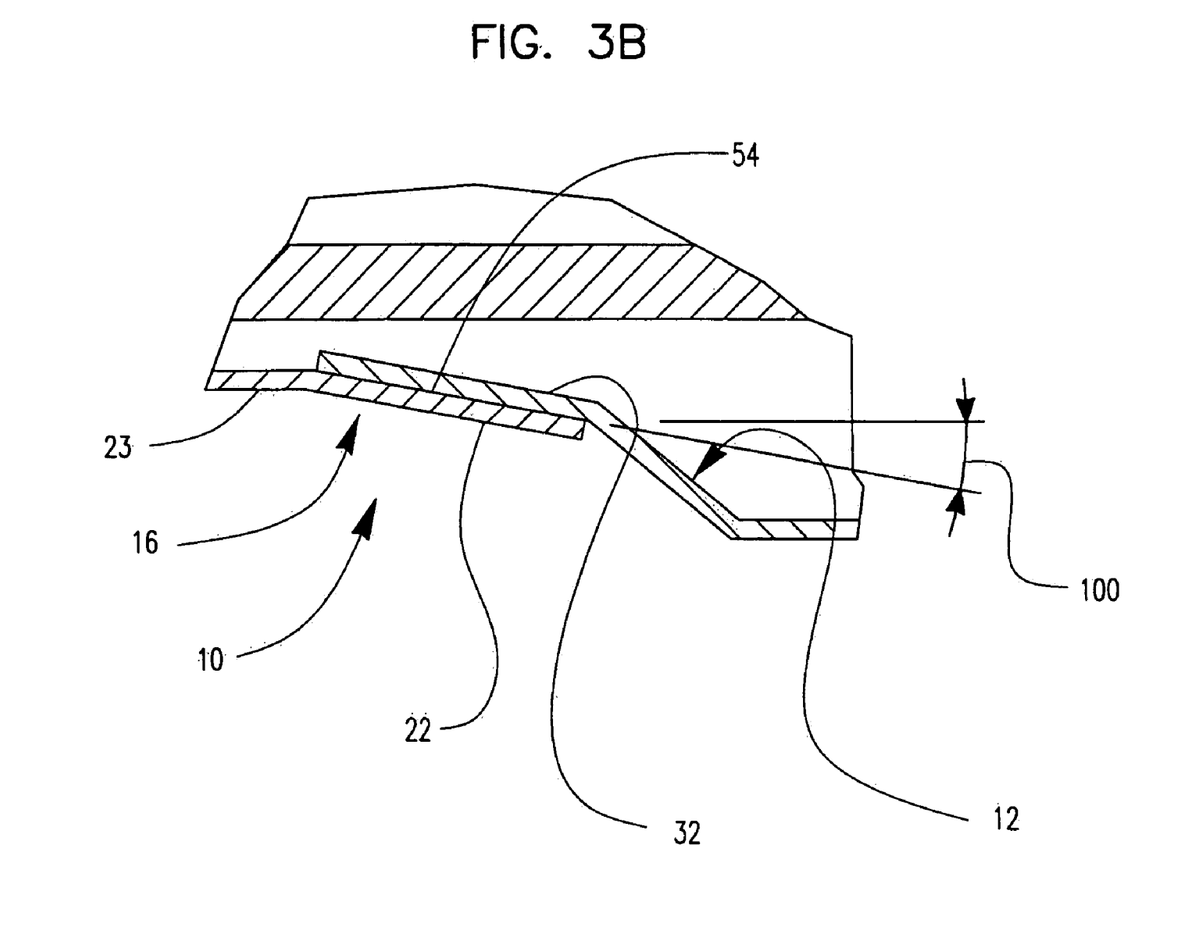
FIG. 3b is an enlarged view of a portion of the catheter assembly shown in FIG. 3 wherein the joint between an outer catheter shaft and the proximal balloon waist is illustrated.

While the catheter 10 is provided with a tapered joint 52 between the distal waist 30 and the inner shaft 14, such as is shown in FIGS. 3 and 3a, such a tapered joint 54 may also be provided between the outer shaft 16 and the proximal waist 32, such as is shown in FIGS. 3 and 3b. In some embodiments joint 54 may be configure to aid in balloon deflation as well.

Where the balloon 12 is engaged to the outer shaft 16, the outer shaft 16 is provided with a frusto-conical shaped engagement region 22. In the same manner as previously discussed in relation to the distal engagement region 20, the proximal engagement region 22 provides the catheter with a self-locking engagement between the outer shaft 16 and the proximal balloon waist 32. Provided that the angle 100 of the taper or frusto-conical region 22 and the substantially cylindrical portion 23 of the catheter shaft 16 is about 25 degrees or less, and in some embodiments between about 1 and about 7 degrees. It should be noted that while in some embodiments the angle 100 is about 25 degrees or less, in alternative embodiments other angles may be used. Any angle that provides the advantageous features described herein may be suitable for use in the formation of the medical device in question.

The balloon 12 and shaft 14 and/or 16 may be of any material desired. For example it is possible to make balloons from a variety of materials that are generally of the thermoplastic polymeric type. Any suitable balloon materials include, but are not limited to: polyamides; polyethylenes, ionomers, ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; copolyesters; thermoplastic rubbers; silicone-polycarbonate copolymers; polyamides; Pebax; Nylon; and ethylene-vinyl acetate copolymers. Orientable polyesters, especially polyethylene terephthalate (PET), are among the preferred materials for forming catheter balloons.

Other references illustrating the materials and methods of making catheter balloons include for example: U.S. Pat. No. 4,47,989 and U.S. Pat. No. 4,456,000 to Schjeldahl et al; U.S. Pat. No. 4,490,421, US Re 32,983 and Re 33,561 to Levy; U.S. Pat. No. 4,906,244, U.S. Pat. No. 5,108,415, U.S. Pat. No. 5,156,612 to Pinchuck et al; and U.S. Pat. No. 5,807,520 to Wang et al; the entire content of each of which being incorporated herein by reference.

Catheter shafts and other components can be made from any suitable material(s).

Methods of assembling the catheter 10 have been referenced above. Assembly of the distal end region of the catheter is depicted in FIG. 2 and such a depiction may be extrapolated to assemble the proximal end region as well. As shown in FIG. 2 the inner shaft 14 is disposed about a mandrel 102 having a region shaped to correspond to that of the tapered engagement region 20. In some embodiments however, the mandrel 102 has a substantially uniform diameter, and the desired tapered shape of the region 20 is a result of a variation in the shape and/or thickness of the inner shaft 14 adjacent to the balloon waist 30.

Once positioned, the balloon 12 is disposed about the shaft 14 and the distal waist 30 is slide over the engagement region 20 to provide the self-locking engagement described above. Once the engagement region 20 and the distal waist 30 are properly overlapped and aligned a laser or other heating device 50 will heat the one or more of the layers to at least its melting point to form the joint 52 between the layers.

Formation of the joint 54 between the outer shaft 16 and the proximal balloon waist 32 may be similarly accomplished however use of a support mandrel may be unnecessary as the inner shaft 14 may act as a supporting member during formation of the joint 54. Alternatively a hollow mandrel and/or sacrificial mandrel may be inserted into the catheter around the inner shaft 14 in order to provide support to the engagement region 22 of the outer shaft 16. Additional methods of supporting the formation of joint 54 are recognized and are incorporated herein.

As indicated above in at least one embodiment in may be necessary to utilize Through Transmission Laser Welding (TTLW) to properly form the joint 52. For example, in embodiments where the shaft 14 and the balloon 12 are constructed of materials which are substantially transparent to the wavelength of the particular form of laser energy which the laser 52 emits, a layer of transition material, selected to absorb the wavelength of the laser, is positioned between the shaft and balloon in order to allow the transition material to be heated by the laser energy and thus conductively heat the surrounding layers to the desired melt point.

In addition to the above, it must be noted that the tapered engagement joints 52 and 54 described herein are not limited exclusively to the frusto-conical shape shown and described. The areas 20 and/or 22 and the corresponding balloon waists 30 and 32 may have any of a variety of complementary shapes, surface features, configurations, etc. Furthermore, while the catheter 10 depicted in FIG. 3 is shown equipped with both tapered joints 52 and 54 the catheter may be provided with only one of the two joints depicted.

As indicated above, it is understood that the method of joint formation and the tapered joints described herein are not limited to use with catheters and their assembly, but may be suitable for use in forming connections between any two overlapping components.

The catheter 10 shown and described herein may be utilized for any of a variety of purposes including but not limited to perfusion, angioplasty procedures, stent delivery, device implantation/retrieval, drug delivery, etc. In at least one embodiment the catheter 10 is equipped with one or more implantable medical devices such as a stent, graft, stent-graft, vena cava filter, expandable framework, etc.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A catheter assembly comprising: an inner catheter shaft having a substantially cylindrical portion and a tapered portion, and an outer catheter shaft having a substantially cylindrical portion and a tapered portion; each tapered portion forming an angle with each cylindrical portion of about 1 degree to about 25 degrees; and a balloon, the balloon having a proximal waist and a distal waist, the proximal waist forming an angle with the cylindrical portion of the outer catheter shaft, the angle being the same as the angle formed by the tapered portion of the outer catheter shaft, the proximal waist sealingly engaged to the tapered portion of the outer catheter shaft and the distal waist sealingly engaged to the tapered portion of the inner catheter shaft; wherein the proximal waist has a length and the distal waist has a length, the entire length of the proximal waist being sealingly engaged to the outer catheter shaft tapered portion and the entire length of the distal waist being sealingly engaged to the inner catheter shaft tapered portion.

2. The catheter assembly of claim 1 wherein the angle is about 1 degree to about 7 degrees.

3. The catheter assembly of claim 1 further comprising a stent, the stent being disposed about a portion of the balloon between the proximal waist and distal waist.

* * * * *

UNITED STATES PATENT AND TRADEMARK OFFICE
CERTIFICATE OF CORRECTION

| | | |
|---|---|---|
| PATENT NO. | : 8,298,179 B2 | Page 1 of 1 |
| APPLICATION NO. | : 11/020540 | |
| DATED | : October 30, 2012 | |
| INVENTOR(S) | : Holman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2023 days.

Signed and Sealed this
Eighteenth Day of November, 2014

Michelle K. Lee
*Deputy Director of the United States Patent and Trademark Office*